(12) United States Patent
Mangino (10) Patent No.: US 9,399,027 B2
(45) Date of Patent: Jul. 26, 2016

(54) ORGAN PROTECTION SOLUTION AND ITS METHOD OF USE

(71) Applicant: VIRGINIA COMMONWEALTH UNIVERSITY, Richmond, VA (US)

(72) Inventor: Martin Mangino, Powhatan, VA (US)

(73) Assignee: Virginia Commonwealth University, Richmond, VA (US)

( * ) Notice: Subject to any disclaimer, the term of this patent is extended or adjusted under 35 U.S.C. 154(b) by 113 days.

(21) Appl. No.: 14/253,982

(22) Filed: Apr. 16, 2014

(65) Prior Publication Data

US 2014/0228436 A1  Aug. 14, 2014

Related U.S. Application Data

(63) Continuation-in-part of application No. 13/589,441, filed on Aug. 20, 2012, now Pat. No. 8,753,806.

(60) Provisional application No. 61/532,153, filed on Sep. 8, 2011.

(51) Int. Cl.
| | |
|---|---|
| *A01N 1/00* | (2006.01) |
| *A61K 31/191* | (2006.01) |
| *A61K 31/08* | (2006.01) |
| *A01N 1/02* | (2006.01) |

(52) U.S. Cl.
CPC ............ *A61K 31/191* (2013.01); *A01N 1/0221* (2013.01); *A61K 31/08* (2013.01)

(58) Field of Classification Search
CPC .... A61K 31/191; A61K 31/08; A01N 1/0221
See application file for complete search history.

(56) References Cited

U.S. PATENT DOCUMENTS

| | | | |
|---|---|---|---|
| 8,067,150 B2 | 11/2011 | Mangino | |
| 2002/0102720 A1 | 8/2002 | Steen | |
| 2008/0187901 A1 | 8/2008 | Doorschodt | |
| 2009/0298043 A1 | 12/2009 | Mangino | |

OTHER PUBLICATIONS

Mosbah I.B. et al., "Efficacy of Polyethylene Glycols in University of Wisconsin Preservation Solutions: A Study of Isolated Perfused Rat Liver", Transplantation Proceedings, 2005, vol. 37, pp. 3948-3950.*
Roskott A. M. et al., "Reduced Ischemia-Reoxygenation Injury in Rat Intestine After Luminal Preservation With a Tailored Solution", Transplantation, Sep. 27, 2010, vol. 90, No. 6, pp. 622-629.*
Muir W., "Fluid choice for resuscitation and perioperative administration", CompendiumVet.com, Compendium: Continuing Education for Veterinarians, Aug. 2009, pp. E1-E10.*
Al-Khafaji A. et al., "Fluid resuscitation", Continuing Education in Anaesthesia, Critical Care & Pain, 2004, vol. 4, No. 4, pp. 127-131.*
[U-2]—Schreinemachers M-C J. M. et al., "Improved preservation and microcirculation with Polysol after transplantation in a porcine kidney autotransplantation model", Nephrol. Dial. Transplant., 2009, vol. 24, pp. 816-824.*
Parrish D. et al., "New low-volume resuscitation solutions containing PEG-20K", Acute Care Surg., 2015, vol. 79, pp. 22-29.*

* cited by examiner

*Primary Examiner* — Satyendra K Singh
(74) *Attorney, Agent, or Firm* — Whitham, Curtis & Cook, P.C.

(57) ABSTRACT

An organ protectant solution which is intravenously administered includes a high concentration of cell-impermeant molecules and at least one oncotic agent. The cell-impermeant molecules preferentially load into the interstitial space and the oncotic agent(s) is/are restricted to the vasculature space. Together, they promote transfer of water from cells to interstitium and into the capillaries, thereby preventing or reducing cell swelling, and maintaining blood circulation and oxygenation of tissues. The organ protectant solution extends the "Golden Hour" for traumatic and/or hemorrhagic shock patients, thereby allowing more time for those patients to reach a point of care facility to receive medical treatment.

3 Claims, 9 Drawing Sheets

A. Vascular Resistance

B. Bile Production

ORGAN PROTECTION SOLUTION AND ITS METHOD OF USE

CROSS-REFERENCE TO RELATED APPLICATIONS

This continuation-in-part application claims priority to U.S. Provisional Patent Application 61/532,153 filed on Sep. 8, 2011, and U.S. patent application Ser. No. 13/589,441, filed Sep. 20, 2012, and the complete contents thereof are herein incorporated by reference.

STATEMENT OF GOVERNMENT INTEREST

This invention was made with partial support of a grant from the United States Department of Defense (Grant Number W81XWH1210599). The U.S. government has certain rights under any patent granted hereon.

BACKGROUND

1. Field of the Invention

The invention is directed to organ protectant solutions, and more particularly, to a solution which prevents or reduces in vivo lethal swelling of tissues and organs during periods of ischemia due to blood loss, trauma or shock, and the resulting lack of oxygen delivery to and oxygenation of tissues and organs. The invention is further directed to a method for treating individuals suffering from rapid blood loss, trauma or shock, thereby extending the period of time during which resuscitation and transportation of such individuals may be safely and successfully conducted in order to provide extended medical or surgical intervention and/or blood transfusion.

2. Prior Art

Initial therapy of trauma and hemorrhage shock centers on effective cessation of bleeding and on the infusion of large volumes (2 to 8 liters) to replace lost blood volume. This is considered necessary to restore normal circulatory functions such as arterial blood pressure, cardiac output, oxygen consumption and renal function. Conventionally, isotonic fluids are used for high volume resuscitation. Many cellular complications and practical limitations have been cited while using high volume fluids for resuscitation. When blood is lost, the greatest immediate need is to stop further blood loss, but the second greatest need is replacing the lost volume. If the fluid volume is maintained, remaining red blood cells may still be sufficient to circulate and oxygenate body tissues for a period of time. In this scenario, it may be possible to reduce or prevent ischemic injury if appropriate medical or surgical intervention can be accomplished.

Recently, resuscitation of hemorrhaged animals and injured patients has been performed with low volume hyperosmotic saline solutions with little success. Glucose or mannitol has been tested with less successful results. Small volume resuscitation has been successfully used in some cases using hyperoncotic albumins or high molecular weight tense state polymerized hemoglobins. The use of hypertonic saline solutions (HTS) or colloid solutions (albumin, HES, Hetastarch, Hextend) have had very limited success in clinical trauma and resuscitation, and, due to their mechanism of action, they do not prevent cell swelling. However, none of these procedures is known to be effective in preventing lethal cell swelling in vivo. Cells, organs, and tissues that suffer from lack of oxygen delivery, as occurs during traumatic shock and hemorrhagic hypovolemia, begin to swell with water because they lose energy dependent volume control mechanisms. In patients suffering from acute hemorrhagic shock and/or trauma, there is substantial intracellular oxygen deprivation, which in turn drops ATP concentration. Due to lack of ATP, the cellular sodium pump fails and free sodium enters the cell, followed by osmotic water movement. Movement of water into the cell causes swelling that leads to organ failure and death. Massive cell swelling further compresses the capillaries and sinusoids and impedes microcirculatory flow through organs and tissues even when the blood pressure is restored after hemorrhage. This is called the "no reflow phenomenon" and it occurs largely from local cell swelling.

This is particularly a problem in battlefield or civilian pre-hospital settings where large volumes cannot be carried and administered to patients in need of rapid paramedical intervention and transport to hospital or surgical treatment centers. There is a so-called "golden hour" of time during which restoration of blood volume and prevention of ischemic injury must be achieved to prevent catastrophic organ failure and death. There is no present day technology to deal with cell swelling and tissue damage to patients experiencing prolonged periods of shock and low volume resuscitation.

SUMMARY

The invention is an organ protectant solution comprising non-toxic cell impermeants and methods for administering it to trauma patients early in pre-hospital settings. The solutions act to favorably readjust the biophysical forces around the ischemic cells and tissues to promote water movement out of the cells and prevent or reverse lethal ischemic cell swelling. Cell-impermeant molecules in the solution load the interstitial space and establish an osmotic gradient from cell to interstitium. Oncotic agents in the solution are restricted to the intravascular space and establish an osmotic or oncotic gradient from interstitium to capillary space to further draw water from the interstitial space into the capillaries and ultimately out of the tissue. The osmotic gradient established by the concomitant use of both impermeants and oncotic agents provides salutatory effects for an individual in need thereof. Water movement into the capillary by the oncotic action of the invention is convectively washed away from the tissue by local blood flow, especially in the microcirculation or capillaries where gas exchange occurs. This potentiates and amplifies the effects of the impermeants alone by convective solvent transfer of the water out of the organ and tissues. Furthermore, movement of interstitial water into the capillary space increases the capillary hydrostatic pressure and provides for more local blood flow and oxygen delivery to the tissues, which reverses the primary low flow problem.

Another embodiment of the invention is an organ protectant solution of cell-impermeants that reduces the cell swelling that underlies ischemic injury. Prevention of lethal cell swelling in vivo will increase the survivability in hemorrhagic shock and trauma patients. The organ protection solution comprises one or more cell impermeants (specific anions and small saccharides) in low volume resuscitation solutions, which are easily administered in the field and can improve resuscitation outcome. The organ protection solution protects organs during severe shock and severe hypotension (acute drop of blood pressure) and/or rapid blood loss due to traumatic injury. Cell swelling can produce lethal injury under any of these conditions and the organ protection solutions described herein target the cell swelling mechanism to make the cells more resistant to damage during low flow states.

Another embodiment is an organ protectant solution of oncotic agents. An organ protectant solution containing oncotic molecules provides the benefit of oncotic pressure within the intravascular spaces. Oncotic pressure within the capillaries promotes transfer of water from the interstitial space into the capillary space and channels cell water away by convective flow movement (blood flow). This action provides the additional benefit of adding fluid to the intravascular space, increasing perfusion pressure and further contributing to maintaining fluid volume and flow in the circulatory system, thereby moving the remaining red blood cells through tissues to oxygenate cells and back to the lungs for $CO_2/O_2$ gas exchange.

In some embodiments, the organ protectant solution is provided as a single use IV infusion solution. The container for an IV infusion solution is typically a lightweight, flexible plastic bag. The amount of solution in the container will typically be less than 2000 ml, and is preferably less than 1000 ml, or more preferably 100-500 ml. When administered to a patient, approximately 100-2000 ml of an organ protectant solution is administered intravenously as quickly as possible when the condition or suspected condition of shock is diagnosed, or after the start of an ischemic event or to protect tissues from a potential ischemic event.

DETAILED DESCRIPTION

To reduce lethal cell swelling of tissues and organs during periods of shock or ischemia due to lack of oxygen delivery and oxygenation, an organ protectant solution containing highly concentrated saccharides and/or anions is provided to the patient as soon as possible. Cell swelling occurs during prolonged periods of shock when medical care is delayed. The organ protectant solution may also be given as a protectant for organs to patients in severe hemorrhagic shock and trauma so as to increase the "Golden Hour" before more definitive medical care can be given (e.g., soldiers on a battlefield before evacuation; patients being pulled from traffic accidents and transported to hospitals by paramedical personnel, etc.).

The organ protectant solutions of the present invention mitigate lethal cell swelling by two modes of action that may be used singly or in combination. The first mode is to preferentially load the extracellular fluid compartment with one or more "impermeant" molecules that are physically able to escape into the extravascular compartment, but which are impermeable to the cell membrane. This preferentially increases the osmotic force outside of the cell, thereby removing cell water accumulation or preventing water from moving into the cell. The second mode of action is to increase the oncotic pressure using one or more oncotic agent. An oncotic agent is a molecule that is restricted to the blood vessel or capillary and pulls water from the extravascular compartment into the vascular compartment. The benefits of the impermeant and oncotic molecules of the invention will become evident with further discussion of the characteristics and properties of each.

As used herein, the terms "impermeant molecules" or "impermeants" are used interchangeably, and refer to a variety of small molecules that are resistant to passing through cell membranes. The cell impermeant molecules are an active ingredient of the organ protectant solutions of this invention, and they may be present alone or in combination with oncotic agents, and/or other suitable constituents (e.g., preservatives, anesthetics, etc.). The molecular weight, size, and charge are specific attributes that allow the molecules to function as cell impermeants. That is, cell impermeants within the practice of the invention have a charge and/or molecular weight which permit them to freely pass across the capillary endothelium and into the interstitial space, but they are too large and/or charged to cross the cell plasma membrane. Thus, they preferentially load into the extracellular fluid compartment where they can exert osmotic effects on both endothelial cells and parenchymal cells.

Examples of cell impermeants with the practice of the invention include specific anions and small saccharides such as sorbitol, gluconate, trehalose, lactobionate, maltitol, raffinose, and combinations thereof. These agents are dissolved in water or a buffer solution (vehicle) such as phosphate buffered saline (PBS), saline, etc., and administered by intravenous infusion (I.V.). They are given in amounts to increase the theoretical extracellular fluid compartment osmolarity of impermeants by 40-100 mOsm/kg. This may require solutions with impermeants of 10-60% by weight and require 250-1000 ml of solution (for a 70 kg adult patient). Of the various small saccharides tested the combination of trehalose-raffinose gave the best results in preventing lethal cell swelling and maintenance of organ vital functions. Other anions and small saccharides may be used as impermeants in the practice of the invention, and organ protectant solutions can include a single impermeant or a mixture of impermeants together with other compounds suitable for the application (e.g., preservatives, anesthetics, etc.). The best impermeants are those with higher molecular weights (e.g., small saccharides or anion with a molecular weight of 342 g/mol or more is preferred). Further, the performance of the organ protectant solution is influenced by the concentration of the impermeants. In general, the organ protectant solutions should have impermeant(s) present at a concentration of 10-60% by weight, and 250-2000 ml (more preferably 250-1000 ml) of organ protectant solution would be required for a 70 kg adult patient (it being recognized that the volume may generally correspondingly be higher or lower depending on the patient size). As discussed in more detail below, the best results were obtained with organ protect solutions including the highest molecular weights at the highest concentration (100 mM or above).

The term "oncotic agent" as used herein refers to a molecule that exerts oncotic pressure, or colloid osmotic pressure, that pulls fluid into the circulatory system. It is the opposing force to capillary filtration pressure and interstitial colloidal osmotic pressure that balances out the tendency for fluid to leak out of the capillaries. In other words, the oncotic pressure tends to pull fluid into the capillaries. Loss of oncotic pressure and an increase in filtration across the capillary, resulting in cell swelling and excess fluid buildup in the tissues. The large majority of oncotic pressure in capillaries is generated by the presence of high quantities of albumin which constitute approximately 80% of the total oncotic pressure exerted by blood plasma on interstitial fluid, but is lost with sudden reduction in blood volume. By definition, oncotic agents are confined to the capillary or intra-vascular space where they can restore sufficient oncotic pressure to maintain circulation of red blood cells that remain in the vessels of an individual suffering from blood loss, trauma or shock.

Examples of oncotic agents suitable for use include various polyethylene glycol (PEG) polymers. Experiments using PEG in organ preservation suggest PEG is nontoxic at high concentrations such as those used in practicing the invention. In some embodiments, PEG-20k is used as the oncotic agent because it provides a size and molecular radius sufficient to stay in the capillary space and act as an oncotic agent. However, it would be clear to one of skill in the art that PEG polymers that are smaller than PEG-20,000, as well as PEG with a larger size such as PEG-35,000 or higher may also be used, as long as the size is sufficiently large enough to stay in the capillary space and act as an oncotic agent. There is evidence to suggest that PEG molecules also possess an as yet unidentified salutary effect on cell membranes during ischemia. The precise mechanism of this benefit is not clearly known, but it has been observed that maintenance of intact cell membranes (or other indicators thereof) is enhanced in tissues and cells treated with the solutions that contain PEG molecules.

The term "volume expanders" as used herein refers to colloids, such as albumin, hydroethyl starch (HES), Hetastarch, and Hextend. The classical example of a volume expander is albumin. Albumin is the most abundant protein in the blood, and has been used in the prior art to expand the volume of circulating blood. Another example is HES, which has been used in clinical trials and as a commercial product (Hetastarch and Hextend) to expand blood volume. However, HES is a "dirty" product with many fragments. The fragmented portion of HES molecules is not necessarily restricted to intravascular spaces, making its effect unpredictable and limiting its usefulness as a clinical volume expander in patients.

There are some prior art organ preservation solutions that use molecules such as lactobionic acid or raffinose. However, these solutions are designed to completely flush and replace the extracellular compartment and will not work as an IV solution (and have not been designed to work as an IV solution). The invention differs markedly from organ preservation solutions of the prior art, in that the invention contemplates a solution formulation and methodology which introduces impermeants into the extracellular space in order to boost the concentrations of the impermeants in the patient to levels that are active for the purposes contemplated herein. The impermeant-based organ protect solutions of the present invention are effectively 5× impermeant solutions that when diluted into the patient's extracellular fluid, will raise the impermeant concentration to an effective level to prevent cell swelling. Other organ preservation solutions, which are not used in the manner described herein, may be viewed as essentially a 1× impermeant solution, and they work only when they completely replace the patient's extracellular fluid. That is, if these solutions were used as low volume solution as described herein (something which they were not designed to do and were not previously used in this manner) the final cell impermeant concentration of the patient will be about 20% of an effective concentration and, therefore, will not work. Thus, it should be clear that other preservation solutions that have some agents which may be viewed as a cell impermeant (e.g., lactobionic acid and raffinose) were not designed to dose the extracellular compartment of the patient as contemplated herein, but were designed to replace it with a synthetic solution (i.e., they are best viewed as organ flush out solutions).

One mechanism of action for the organ protectant solutions of the present invention is to transfer water from cells to the interstitial spaces by loading the interstitial spaces with impermeants. A second mechanism of action is the transfer of water from the interstitial spaces into the vasculature, by means of oncotic molecules or agents that are restricted to the vessels and capillaries. This two-step transfer helps to prevent lethal cell swelling. The intracellular concentration of ATP drops in cells when they are deprived of oxygen. Consequent to this is the reduction or arrest of all chemical processes that require intracellular energy (ATP). One of those processes is active cellular volume control. Volume control occurs when the cell actively pumps sodium (Na) out of the cell. This also removes water. When these sodium pumps fail, due to lack of ATP, free sodium enters the cell down an electrochemical gradient, which is followed by electrogenic chloride, and then by osmotic water movement. This causes lethal cell swelling that causes direct cellular injury by cell membrane and mitochondrial injury, and causes further reductions in capillary blood flow and oxygenation (termed the NO REFLOW PHENOMENON) by swelling-induced compression of the microcirculatory exchange vessels (capillaries).

Figure 1:
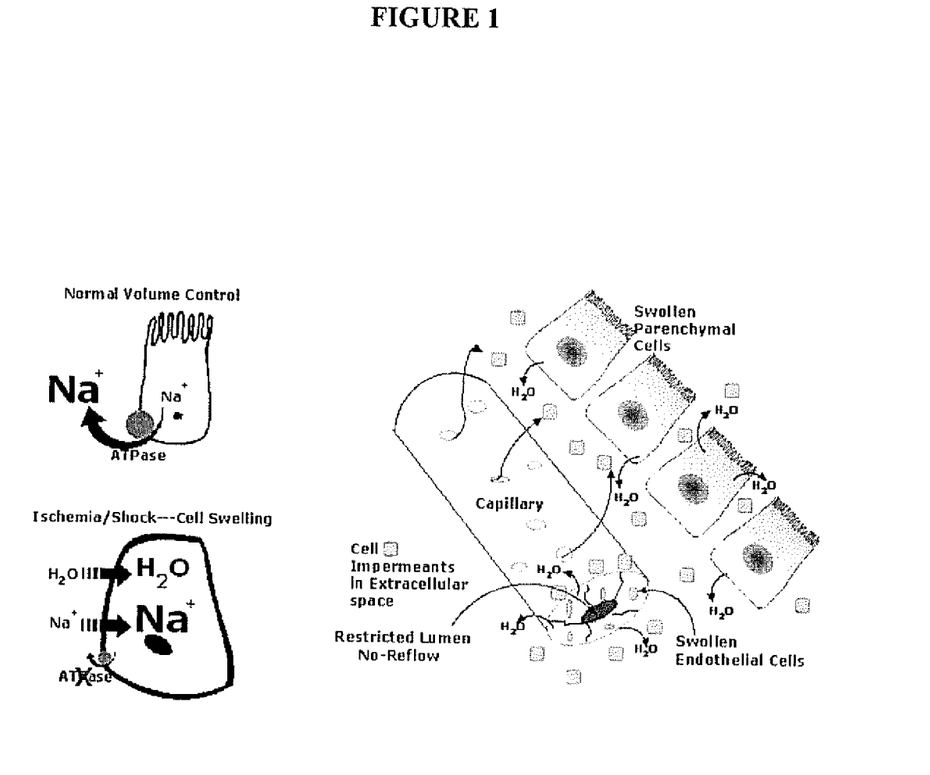
FIG. 1 is a schematic drawing which illustrates the mechanism of action of the organ protectant solutions

FIG. 1 schematically illustrates the mechanism of action of the organ protectant solutions provided by impermeants. The top left of FIG. 1 shows normal volume control in a cell is achieved by pumping sodium out of the cell, while, in contrast, the bottom left of FIG. 1 shows that when the sodium pump stops working due to lack of ATP, the sodium is not pumped out of the cell and the cell enlarges by osmotic water movement into the cell. The right side of FIG. 1 shows that the organ protectant solutions load the extracellular fluid compartment with molecules that are impermeable to the cell membrane. This increases the osmotic forces outside the cell, which in turn either or both removes water from the cells or prevents water from moving into the cell. As shown in FIG. 1, the impermeant molecules have a charge and/or molecular weight that permit them to freely pass across the capillary endothelium and into the interstitial space, but they are too large and/or charged to cross the cell plasma membrane. Addition of oncotic agents that are restricted to the capillary (or other vasculature) promotes transfer of water from the interstitial space into the capillary. It is then incorporated into the circulation, with the added benefit of contributing to the fluid volume therein.

A preferred embodiment of the invention is an organ protectant solution that is suitable for administration to an individual suffering from blood loss, trauma or shock. The clinical introduction of the solutions to reduce or prevent lethal cell swelling is via intravenous administration of organ protectant solutions. Organ protectant solutions can be administered to soldiers on a battle field or civilians in the field (e.g., at the scene of an automobile accident) during the low volume state while awaiting more comprehensive medical care. The organ protectant solutions, through preventing lethal cell swelling, buy precious time and allow for trauma care for the shocked patient.

The organ protectant solutions of this invention (i.e., cell impermeant-based solutions) can be used whenever cell swelling due to ischemia may be a problem, for instance, during hemorrhagic shock and trauma before definitive resuscitation can occur. More broadly, the organ protectant solution may also be used in any hospital, birthing, surgical, or primary medical care center, where unexpected bleeding or hemorrhage might occur as a consequence of a medical or surgical treatment.

Accordingly, organ protectant solutions have exemplary uses in:

1. Combat casualty care: The military use for organ protectant solutions may indeed be great. Most injuries and deaths on the battle field are due to severe hemorrhagic shock and trauma secondary to blast injury and high energy projectile impacts. Soldiers must be treated in harsh conditions with low volume resuscitation using simple solutions that are chemically stable in extreme temperature conditions. Cell impermeant-based low volume resuscitation solutions fit the bill. They have been shown in preliminary studies to extend the time that a subject can remain in the low volume state, which theoretically could extend the "Golden Hour" and allow higher percentages of severely injured soldiers to survive until they reach more definitive trauma care at forward medical hospitals after evacuation from the field. Increasing the "Golden Hour" time 2-5 fold is possible and this may have a huge impact on mortality and morbidity.

2. Civilian trauma care: Severe hemorrhagic shock and trauma in civilian situations may typically arise from motor vehicle crashes, recreational accidents, and urban violence, among others. Severe hypotension and shock, even when successfully resuscitated, can often lead to secondary hemodynamic problems, infection, and multiple organ failure in the surgical intensive care unit. These patients often die from these secondary complications and there are no good effective treatments. Cell impermeant therapy, given at the time of initial resuscitation, may lower the incidents of these lethal secondary complications or reverse them if they are also administered at or around the time of their onset in the field. The organs that are particularly vulnerable in shack include the splanchnic organs (liver, intestines, and pancreas) and the lungs. Protecting these and other organs from lethal cell swelling may be key to mitigating secondary complications and multiple organ failure.

3. Sudden blood loss or hemorrhage occurring unexpectedly as a result of an otherwise routine medical or surgical procedure. Even when a surgical procedure is expected to be uneventful, complications or iatrogenic injury may occur and cause uncontrolled bleeding or loss of blood pressure. While some situations may include provision for rapid blood transfusion, many do not, particularly when conducted in ancillary or satellite facilities, such as a same-day or outpatient surgical center or birthing center. When a patient's condition becomes acutely grave, the typical course of action is to transport the patient to a hospital or trauma center where an escalated level of care can be provided. It is contemplated that administration of an organ protectant solution would provide a means of counteracting shock and reducing ischemia during the period of time when a patient is still in the ancillary medical center and during transport to a full-service medical center.

The following examples demonstrate the use of cell impermeants with or without oncotic agents in organ protectant solutions for hemorrhagic shock, trauma, and extension of the time during which an individual may be successfully resuscitated, treated and/or transported to a site where medical or surgical treatment can be provided, and more clearly show that the organ protectant solutions of the invention prevent or reduce lethal cell swelling. The Examples are provided to illustrate various embodiments of the invention, but should not be considered as limiting in any way.

EXAMPLES

Example 1

Exemplary Formulation of Cell-Impermeant-Based Organ Protectant Solution

Table 1 presents the formulation of one example of a cell impermeant-based organ protectant solution according to the present invention. As discussed herein, the precise formulation of the cell impermeant-based organ protectant solution can vary within the practice of the invention. Specifically, the organ protectant solution should have one or more cell impermeants dissolved or dispersed in a pharmaceutically acceptable vehicle. The cell impermeant(s) will have a charge and/or molecular weight which permits them to freely pass across the capillary endothelium and into the interstitial space of a subject, but they are too large and/or charged to cross the cell plasma membrane such that they preferentially load into the extracellular fluid compartment where they can exert osmotic effects on both endothelial cells and parenchymal cells. They are given in amounts to increase the theoretical extracellular fluid compartment osmolarity of impermeants by 40-100 mM. This may require solutions with impermeants of 10-60% by weight and require 250-1000 ml of solution (for a 70 kg adult patient).

TABLE 1

| Cell Impermeants | Concentrations | g/L (1.5M) |
|---|---|---|
| Sorbitol | 0-1.5M | 273 |
| Gluconate (Na) | 0-1.5M | 294 |
| Trehalose | 0-1.5M | 513 |
| Raffinose | 0-1.5M | 891 |
| Lactobionate (Na) | 0-1.5M | 597 |
| Maltitol | 0-1.5M | 516 |
| Combinations | 0.4-1.5M Total | — |

Administration of approximately 0.5 liter is recommended per adult patient (assumed to be approximately 75 kg) to achieve the desired effect. The vehicle is phosphate buffered saline (PBS).

Example 2

Exemplary Method of Administration of the Cell Impermeant-Based Organ Protectant Solutions The general rule of thumb should be to start administration of the organ protection solutions as quickly as possible after the start of the ischemic event (e.g., hemorrhage due to trauma, cardiovascular collapse in shock). Give the solutions through an intravenous catheter like any I.V. fluid. For administration during shock, these solutions can be part of the resuscitation fluids. The solutions can be stored in convenient bags typically used I.V. fluid, such as Viaflex, for storage, transportation, and use. Typical administered volumes may be in the range of, for example, 100-2000 ml, 100-1000 ml, 100-500 ml or 100-250 ml per patient, depending on the body mass and condition of the patient and the formulation of the solution. They also may be administered by constant infusion in the intensive care unit (ICU) during recovery from surgery and resuscitation. Alternatively, small amounts, such as 100-200 ml can be injected slowly into an IV line, vein or artery using a needle of suitable gauge and a disposable syringe.

In any of the above described situations, it is also possible that there may be large numbers of victims, necessitating triaging decisions that require some patients wait longer for transport to medical care. It is contemplated that prophylactic administration of organ protectant solution to patients who are identified for delayed treatment may be a prudent emergency treatment protocol if they are hypotensive and hypoperfused.

Example 3

Determination of Optimal Impermeant Molecules in an Organ Preservation Model

A series of experiments were performed to explore the optimal impermeant effect of a family of likely useful impermeants. The variables are molecular species of impermeant, concentration (in the extracellular space), and time of administration. For these experiments, the impermeants used included specific anions and small saccharides such as sorbitol, gluconate, trehalose, lactobionate, maltitol, raffinose, and combinations of the same. These agents were dissolved in water of buffer solution such phosphate buffered saline and used in an in vitro tissue culture study.

Figure 2:
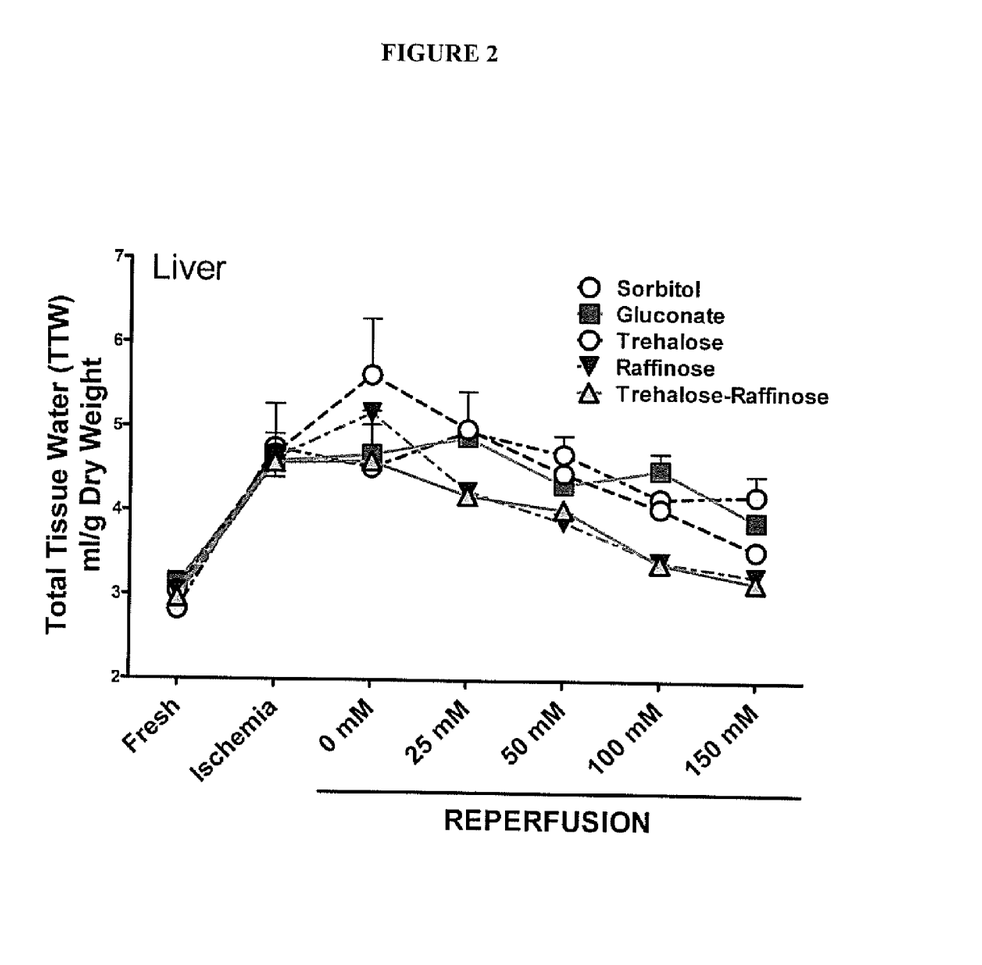
FIG. 2 is a graph showing the effects impermeants have on swelling of liver slices.

FIG. 2 illustrates the effect of various impermeants on cell swelling of liver slices. The outcome variable was cell swelling of liver tissue slices exposed to periods of warm ischemia and reperfusion to mimic the conditions that a DCD donor liver would encounter in order to determine which solutions would minimize in vivo cell swelling. For these experiments, the best impermeant solution had the highest molecular weight and highest concentration (e.g., trehalose has a molecular weight of 342 g/mol, and best results were obtained with concentrations of 100 mM or above). However, combinations of high and moderate molecular weight impermeants also proved to work well.

In this model, liver tissue weight almost doubled after ischemia due to cell swelling from water accumulation. Cell impermeants in the extracellular space largely prevented or attenuated this increase. From these in vitro data, an optimized impermeant for in vivo treatments may include mixtures of trehalose and raffinose at about 50 mM each.

Figure 3:
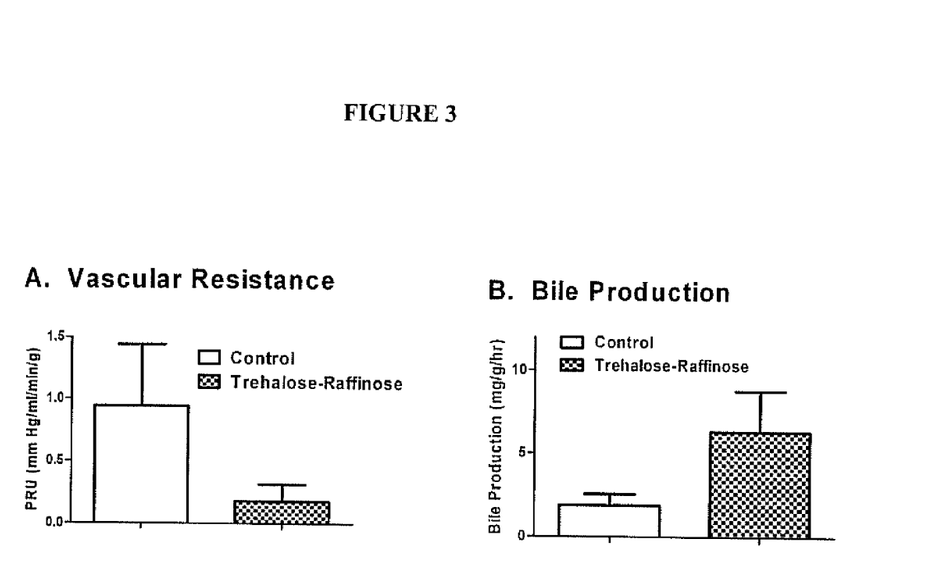
FIG. 3A is a bar graph illustrating measurements for vascular resistance in a donation after cardiac death (DCD) model for liver donation.
FIG. 3B is a bar graph illustrating measurements for bile reduction in a DCD model for liver donation.

FIGS. 3A and 3B show the effect of cell-impermeant based organ protection solutions on a DCD model for liver donation to determine parameters for preventing liver failure in vivo in trauma patients. Adult donor rats were anesthetized and a bilateral pneumothorax was induced, which caused heart failure in 2 minutes. Then, 30 minutes of time was allowed to elapse to simulate warm ischemia in the DCD patients. At the time of heart failure, animals were assigned to either a control group that received about 3 ml of PBS vehicle I.V. over 10 minutes or an experimental group that was given about 3 ml of a trehalose and raffinose solution in PBS (about 750 mM each), I.V. over 10 minutes. Each animal also was given heparin and phentolamine at the time of cardiac death. After 30 min of in-situ warm ischemia, the liver was harvested and flushed with UW solution and cold stored for 24 hours. The livers were reperfused on an isolated perfused liver preparation (IPL) in-vitro for 60 minutes to assess post-reperfusion liver function (preservation injury). FIGS. 3A and 3B show vascular resistance and bile production for both groups, respectively.

FIGS. 3A and 3B show that treating DCD liver donors with impermeants in the peri-death period resulted in significant reductions in vascular resistance to flow and significantly increased bile synthesis at reperfusion (transplantation). Bile production in the early post-reperfusion period (the first hour after transplantation) is a highly predictive marker for later liver viability and life-saving function. These results clearly indicate less preservation injury with the use of cell impermeants in DCD donors. Since the end result of the experiment was a higher quality donor organ, the data are predictive for determining the likelihood of preventing organ failure when the solutions are used to treat individuals suffering from blood loss, trauma or shock.

Example 4

Hemorrhagic Shock Model in Rodents

Gluconate was administered in the organ protectant solution (e.g., a low volume resuscitation (LVR) solution with cell impermeants according to the present invention) in order to achieve a theoretical gluconate concentration of about 60 mM in the extracellular fluid compartment (subsequent experiments have shown that about 100 mM is probably optimal). The idea of low volume resuscitation is to give the shocked patient small volumes of intravenous fluids to prolong the time on the field to allow for rescue and transport to a forward hospital where more definitive resuscitation can occur (due to fewer resource limitations). The purpose of the addition of the cell impermeants to the LVR solution (usually saline) was to increase this "down time" further, effectively increasing the tolerance to the low flow state and making it more likely that the patient can survive the wait to the hospital. Essentially, the objective is to increase the "Golden Hour".

Figure 4:
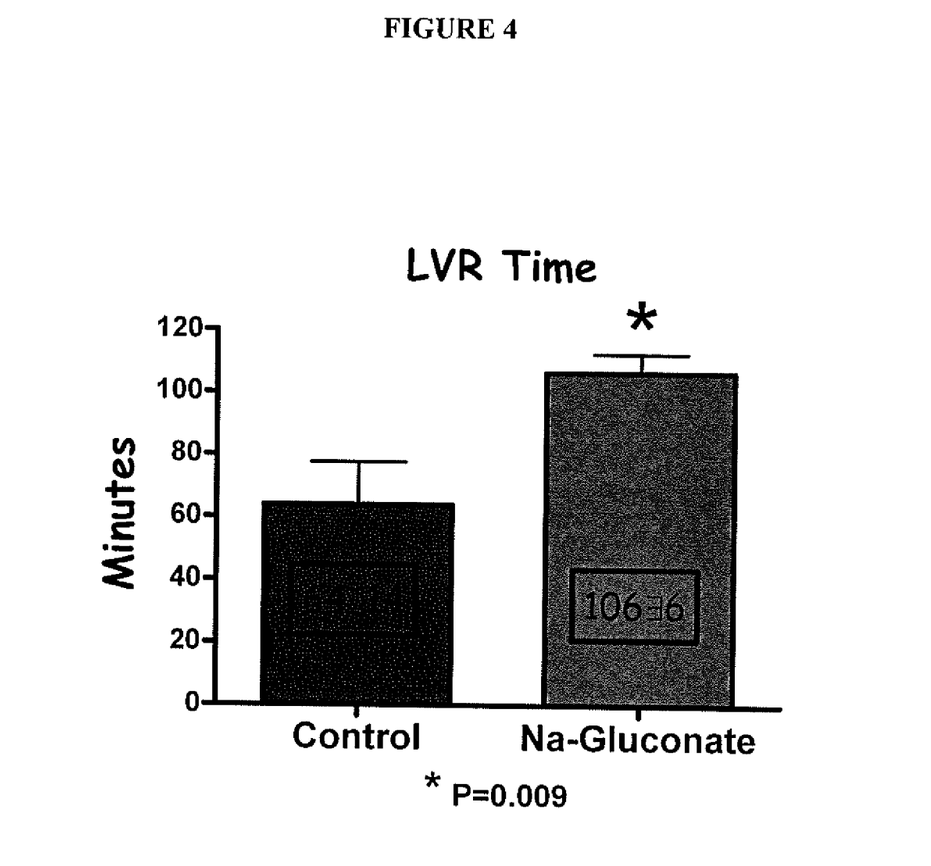
FIG. 4 is a bar graph illustrating increases in the low volume resuscitation time with cell impermeants in an in vivo model.

FIG. 4 shows measurements of the LVR time period, a measure of the "Golden Hour". In shock experiments, the time that the control animals could remain in the low volume state (after LVR administration) was 64 minutes. However, gluconate added to the LVR solution significantly enhanced the LVR time to over 106 minutes. This means that these subjects were able to stay safely in the low volume state for much longer periods. In practical terms, they can wait longer for transport and full resuscitation, yet presumably have a higher chance of survival.

Figure 5:
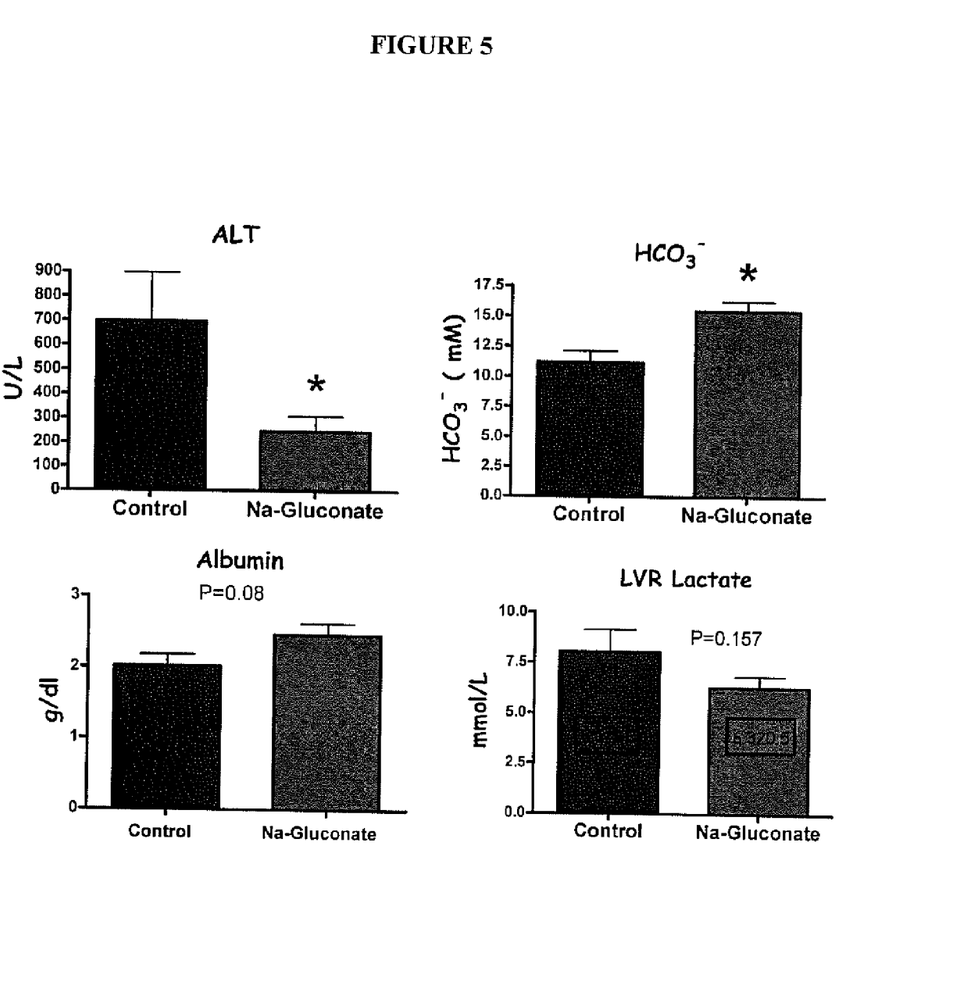
FIG. 5 is a collection of bar graphs which show the effect of adding gluconate to low volume resuscitation (LVR) solution in liver enzymes, albumin, and metabolic acidosis.

In support of the determination that the LVR time is extended, gluconate-treated subjects also had less liver injury and better metabolism 24 hours after shock and resuscitation. This is shown in FIG. 5, which illustrates the beneficial effect of adding gluconate to LVR solution on liver enzymes, albumin, and metabolic acidosis. Liver enzymes were lower and albumin was higher in the gluconate group. Likewise, there was less metabolic acidosis in the gluconate group. Furthermore, the subjects in the gluconate group were kept in the low volume state much longer than the controls. Despite enduring much more hypotension (because the gluconate increased the low volume time), their condition as demonstrated by all parameters measured in FIG. 5 was improved the next day, compared to the controls.

Example 5

Use of Combinations of Impermeant Molecules and Oncotic Agent(s) in Organ Protectant Solutions In this example, an oncotic agent is added to the impermeants to observe and test the proposed convective amplification effect. Therefore, studies were conducted using the oncotic agent polyethylene glycol-20,000 (PEG-20k) with impermeant-based low volume resuscitation solutions disclosed above. Three groups of shocked rodents (described below) were included. LVR is initiated in all animals when plasma lactate reaches 10 mM, which is used as the definition of shock.
1. Saline controls: These animals received only saline as the low volume resuscitation fluid. The amount of LVR solution was 20% of the calculated blood volume, which is an equivalent of 1 liter in an adult human.
2. Impermeants-based LVR solution: These animals received combinations of the impermeants gluconate, raffinose, and trehalose at 10-25%, given at a volume of 20% of calculated blood volume.
3. PEG-20k-based impermeant LVR solution: This LVR solution contained both 10% PEG-20k and 15% gluconate (impermeant). For this group, the volume administered was cut in half to 10% of the calculated blood volume. This is equivalent to 0.5 liters for an adult human, and is within the dose range for a human with a body weight of 70-75 kg.

The main endpoint of this study was the low volume resuscitation (LVR) time, which is an indicator of the tolerance of the patient to withstand the low volume state during hemorrhage and trauma. The longer the LVR time, the longer an injured or traumatized individual can remain in the field before definitive medical treatment must occur. It is an approximation of the concept of the so-called "Golden Hour". As the golden hour increases, so does the ability to withstand periods of shock in the field before definitive resuscitation at a medical center or field hospital is required. The converse is also true. Specifically, a longer golden hour greatly improves physiological function when a patient arrives at a hospital or trauma care center with conventional transport times. In these studies, the low volume resuscitation time is the time measured from the start of the LVR solution until the time when the plasma lactate level climbs back up to the critical value of 10 mM. At this time, full resuscitation must be given to avoid death. The invention provides an organ protectant solution that can expand the LVR time and provide more time for safe evacuation and definitive treatment at a qualified medical center of forward field hospital. It is also noteworthy that the combination of impermeant and oncotic molecules in the organ protectant solution provided better results with approximately half the volume of solution administered, compared to the volume of saline solution or impermeant solution.

Figure 6:
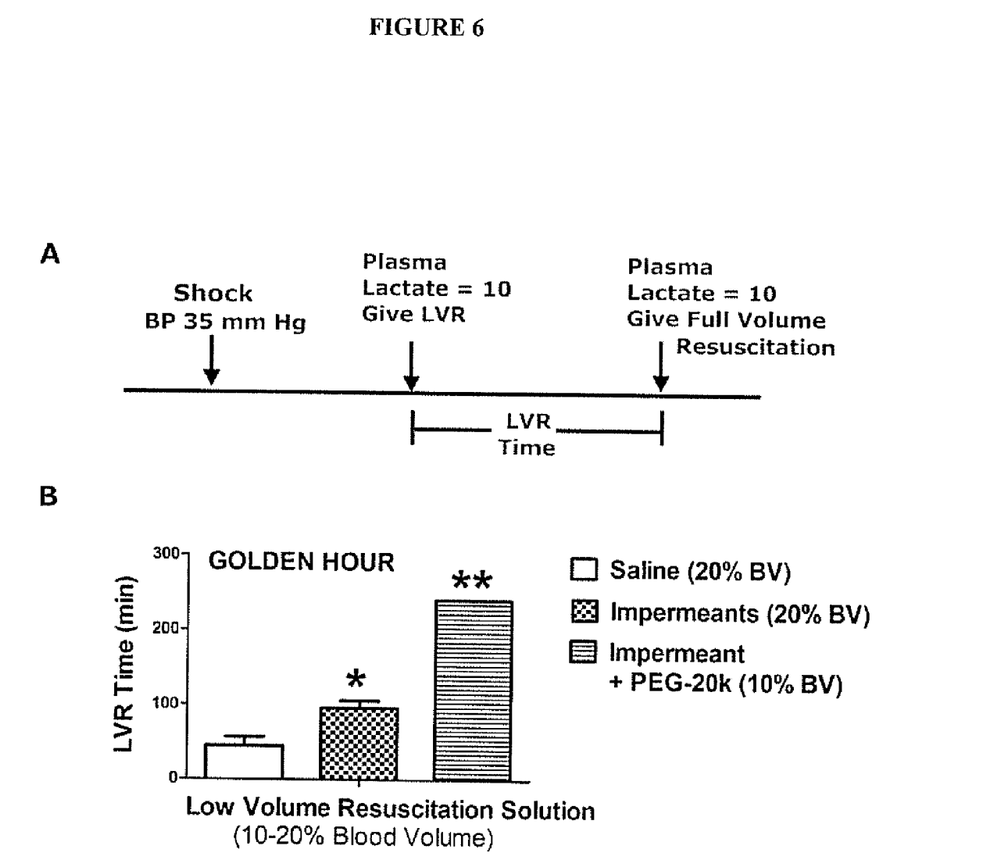
FIG. 6A is a timeline illustrating the concept of LVR time.
FIG. 6B is a bar graph showing LVR times observed in 3 experimental groups of shocked animals.

FIG. 6A shows a timeline illustrating the concept of LVR time progression, relative to blood pressure (BP) and plasma lactate as indicators of shock. FIG. 6B shows the actual LVR times observed in the three experimental groups of shocked animals. Animals receiving the PEG-20k-based impermeant LVR solution maintained a lactate level of 2.0 mM for 5-fold longer period of time beyond that animals receiving saline solution, and greater that 2-fold longer than animals receiving impermeants-based LVR.

Figure 7:
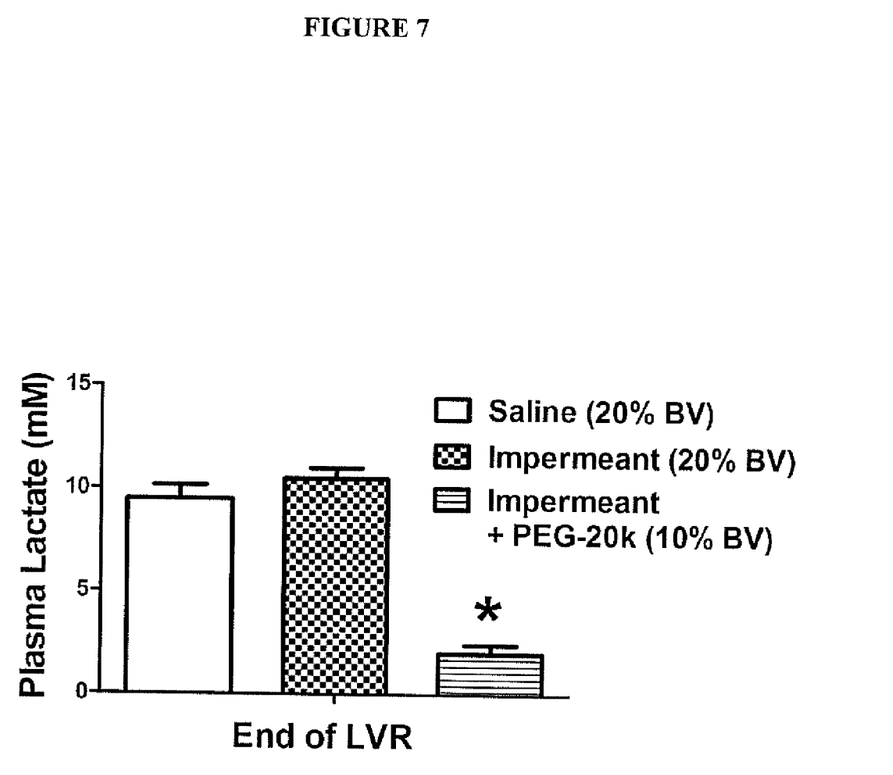
FIG. 7 is a line graph showing mean arterial blood pressure (MAP) measured in 3 experimental groups of shocked animals.

Example 4, showing the effects of a solution comprising impermeant molecules, is recapitulated in this study in the second group of subjects. The impermeant-based LVR solution doubled the LVR time seen with the saline controls in the first group of subjects. However, the impermeant effect was dramatically potentiated in the third group where PEG-20k (10%) was added to the impermeants. The LVR time was increased 5 fold above the saline control group. Furthermore, this was accomplished with only ½ of the volume (10% of the calculated blood volume compared to 20% in the other groups). Finally, the 4 hour LVR time was an artificial cut off since the real LVR time is much longer but still unidentified. The LVR times are defined by the time required for the patient to build more oxygen debt after administration of the LVR solution, as measured by the target lactate level of 10 mM. As shown in FIG. 6B, the PEG-20k-treated animals, which had a 5 fold higher LVR time, still had a plasma lactate of only 2 mM and were far away from the 10 mM target, shown in FIGS. 6B and 7. How much longer the animals could have remained in the low volume state until their lactate values reached 10 mM was not determined. However, this experiment demonstrates that administering a solution of both impermeant molecules and oncotic agents maintains protection from tissue and organ damage for at least 5 times as long as saline solutions and more than twice the time as can be achieved with impermeant-based solutions. In practical terms, this means that the time for resuscitation, treatment, and/or transport to a trauma center has been extended at least 5-fold, increasing from less than 45 minutes, to greater than 4 hours with administration of a solution of both impermeant molecules and oncotic agents.

Figure 8:
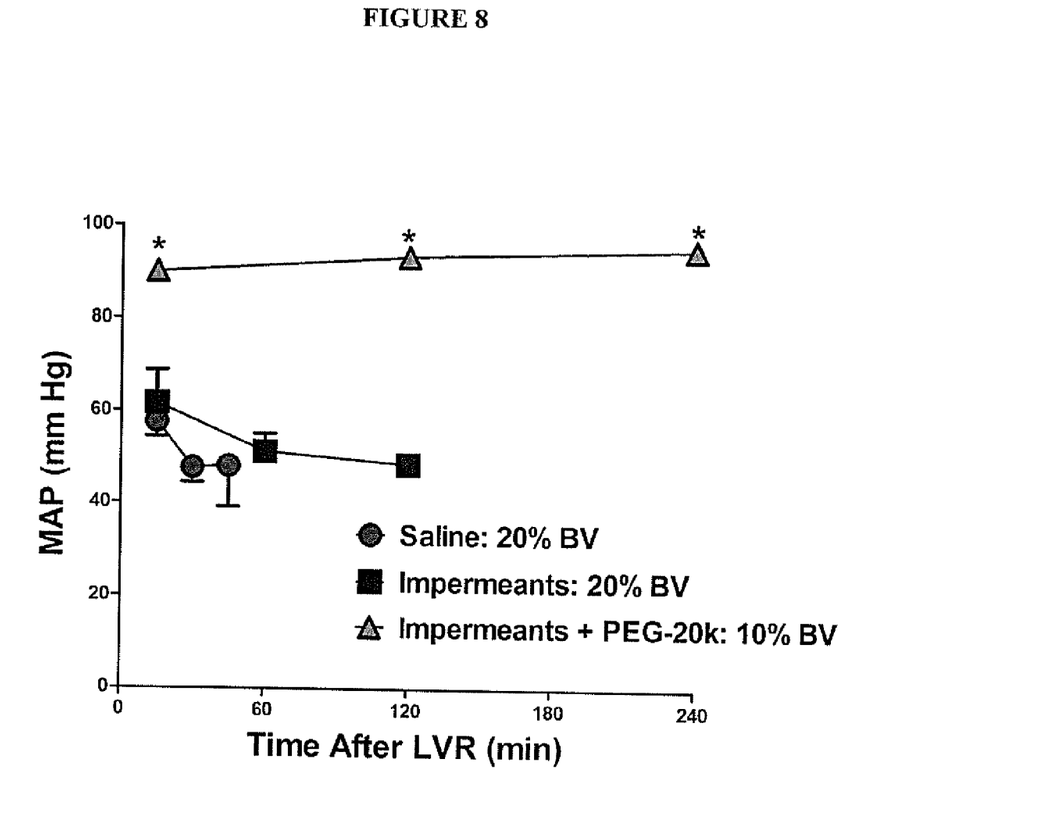
FIG. 8 is a bar graph showing plasma lactate measured in 3 experimental groups of shocked animals at the end of the experimental LVR.

Maintenance or restoration of blood pressure is a critical indicator of successful resuscitation and competent circulation, which is needed to oxygenate tissues and prevent ischemic injury. The mean arterial blood pressure (MAP) during the LVR period was much higher in the PEG-20k group, relative to the control and the impermeant group. FIG. 8 shows that while the other groups had a low and falling blood pressure during the LVR period, the PEG-20k group maintained blood pressure to normal values during LVR (with half the I.V. volume, relative to control saline or impermeant alone groups). In real life terms, this suggests a scenario where a severely shocked patient losing 50% of their blood volume that is given 500 ml of a PEG-20k-based impermeant LVR solution (I.V.) can remain in the field for 4-5 hours before being transported to the hospital where his cardiovascular and metabolic signs on arrival will still be essentially normal. The same patient given twice as much saline in the field (the current standard of care) will die from the same blood loss in only 45 minutes. Typically, the solution would be administered as an IV drip solution, with a volume of 500-2000 ml for an adult patient. These data also indicate that smaller volumes, such as 100 ml, 200 ml, 250 ml, 300 ml, or 400 ml would still extend LVR time and allow successful resuscitation and maintain circulation for a sufficient period of time to transport a patient to a site where definitive care can be provided.

Example 6

Use of PEG as an Oncotic Agent(s) in Organ Protectant Solutions

In this example, an oncotic agent is used alone to observe and test the effect of the colloid alone and to test different molecular species of PEG where lower molecular weight polymers may possess both impermeant and oncotic properties, and therefore, may be used without other impermeant agent. Therefore, studies are conducted using the oncotic agent polyethylene glycol-20,000 (PEG-20k) and other polymers with lower molecular weight (PEG-10,000) or with higher molecular weight (PEG-35,000) as the low volume resuscitation solutions disclosed above. Groups of shocked (plasma lactate of 10 mM) rodents include:
1. Saline controls: These animals receive only saline as the low volume resuscitation fluid. The amount of LVR solution is 20% of the calculated blood volume, which is an equivalent of 1 liter in an adult human.
2. Impermeants-based LVR solution: These animals receive combinations of the impermeants gluconate, raffinose, and trehalose at 10-25%, given at a volume of 20% of calculated blood volume.
3. PEG-20k-based impermeant LVR solution: This LVR solution contains both 10% PEG-20k and 15% gluconate (impermeant). For this group, the volume administered is cut in half to 10% of the calculated blood volume. This is equivalent to 0.5 liters for an adult human, and is within the dose range for a human with a body weight of 70-75 kg.
4. PEG-20k-based LVR solution: This LVR solution contains 10% PEG-20k alone and demonstrates the effect of just the PEG without the other impermeants.
5. PEG-10k-based LVR solution: This LVR solution contains 10% PEG-10k alone and tests the effect of just the PEG without the other impermeants. A lower molecular weight of PEG demonstrates the effect of a hybrid impermeant and colloid effect alone.
6. PEG-35k-based LVR solution: This LVR solution contains 10% PEG-35k alone and tests the effect of just the PEG without the other impermeants. This size PEG provides only oncotic effects with no impermeant effects since the molecule stays within the capillary.

These studies can be used to identify the weight of PEG that may be used alone to achieve a hybrid impermeant and oncotic effect as well as describe the salutary effects of just the oncotic effect alone in PEG species that have pure oncotic effects.

Example 7

Figure 9:
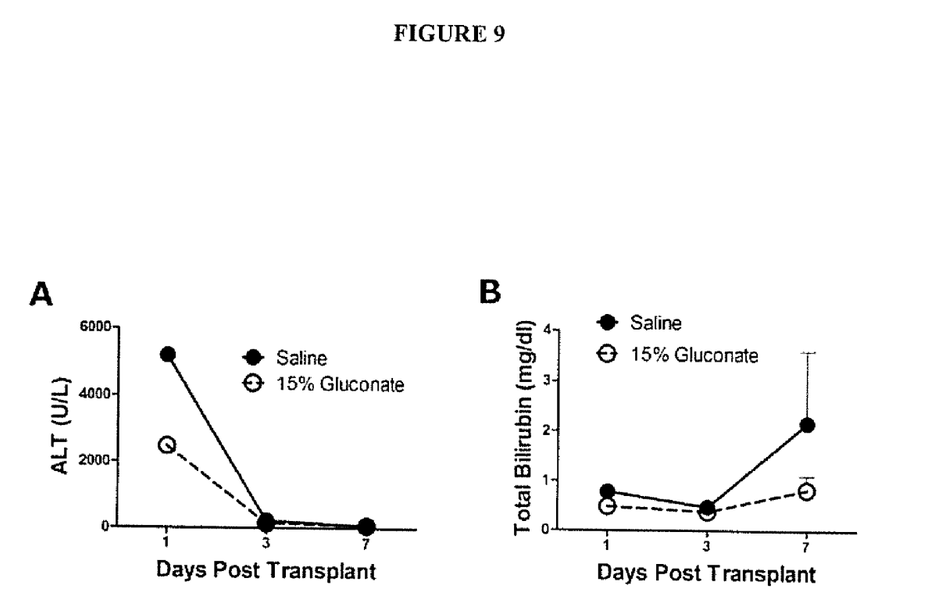
FIG. 9A is a line graph showing enzyme release (liver injury) after liver transplantation in control (saline) and impermeant treated (15% gluconate) donors before donation after cardiac death (DCD).
FIG. 9B is a line graph showing total bilirubin levels after liver transplantation in control (saline) and impermeant treated (15% gluconate) donors before donation after cardiac death (DCD). Rising bilirubin is an indicator of the development of ischemic cholangiopathy in DCD liver transplant recipients.

Use of the Impermeant Organ Protectant Solutions to Prevent the Early Signs of the Development of Ischemic Cholangiopathy in DCD (Donation after Cardiac Death) Livers Used for Transplantation In this example, an impermeant solution containing any one or a mixture of listed impermeant molecules (gluconate, raffinose, trehalose, sorbitol, lactobionic acid, maltitol) with or without an oncotic agent (PEG-20k or higher molecular weight) is infused into a DCD organ donor at the time of cardiac death or shortly thereafter (about 1-2 liters of solution). The solution may be circulated by continuing CPR. The liver and other organs are retrieved later, after experiencing 30-90 min of warm ischemia time, using conventional surgical techniques and cold organ flush solutions (UW solution). The livers and other organs are either cold stored or machine perfused using UW based solutions in the conventional way. The liver is transplanted and adequate function returns. The chance of ischemic cholangiopathy developing days or weeks later are lessened or prevented by the use of the impermeant organ protectant solutions. Studies done in adult rats show that the early liver lysis that occurs after transplantation (preservation injury) is lessened in the impermeant group, shown in FIG. 9A. FIG. 9B shows that DCD livers that were transplanted into recipient rats did not show signs of early ischemic cholangiopathy when treated with the protectant solutions since the total bilirubin levels did not significantly rise one week after transplantation, relative to the controls that were not treated at the time of liver retrieval. These data in this example indicate that the organ protectant solutions are able to salvage DCD livers and prevent or attenuate the development of ischemic cholangiopathy, which currently limits the use of DCD livers in clinical transplantation today.

From the examples and description provided herein, it is clear that addition of an appropriate colloidal oncotic agent to the impermeant LVR solution dramatically amplifies the impermeant effect and increases the "Golden Hour" 5-fold at half of the administered volume. This is critical in battlefield or civilian pre-hospital settings where large volumes cannot be carried. Administration of an organ protectant solution containing impermeant and oncotic molecules also dramatically improves patient cardiovascular and metabolic function after prolonged periods of shock and low volume resuscitation.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:
1. An organ protectant solution formulated as a single use infusion, comprising:
   one or more of gluconate, raffinose, and trehalose at 10-25% by weight, polyethylene glycol polymers (PEG) with a molecular weight of 20,000 daltons at 5-10% by weight, and
   a pharmaceutically acceptable carrier,
   wherein the solution of the one or more of gluconate, raffinose, and trehalose, the PEG, and the pharmaceutically acceptable carrier is present in a container as a single use infusion suitable for administration to a human, and wherein volume of the solution is no more than 2000 ml.
2. The organ protectant solution of claim 1, wherein the volume of the solution is no more than 500 ml.
3. The organ protectant solution of claim 1, wherein said PEG is at 10% by weight.

* * * * *